United States Patent
Burbank et al.

(10) Patent No.: US 7,686,817 B2
(45) Date of Patent: Mar. 30, 2010

(54) OCCLUSION DEVICE FOR ASYMMETRICAL UTERINE ARTERY ANATOMY

(75) Inventors: Fred H. Burbank, Laguna Niguel, CA (US); Greig E. Altieri, Laguna Beach, CA (US); Michael L. Jones, San Clemente, CA (US); Ed Olson, Lake Forest, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 1639 days.

(21) Appl. No.: 10/721,857

(22) Filed: Nov. 25, 2003

(65) Prior Publication Data
US 2005/0113634 A1    May 26, 2005

(51) Int. Cl.
A61B 17/42    (2006.01)
(52) U.S. Cl. .......................................... 606/119
(58) Field of Classification Search ................ 606/157, 606/158, 190–193, 198, 205–208, 105, 90, 606/119, 120, 151; 604/36, 37; 600/201, 600/214–216, 210, 211; 700/245
See application file for complete search history.

(56) References Cited

U.S. PATENT DOCUMENTS

| | | | |
|---|---|---|---|
| 2,400,251 | A | 5/1946 | Nagel |
| 3,209,753 | A | 10/1965 | Hawkins et al. |
| 3,411,505 | A | 11/1968 | Nobis |
| 3,777,740 | A | 12/1973 | Hokanson |
| 3,779,248 | A | 12/1973 | Karman |
| 4,120,302 | A | 10/1978 | Ziegler |
| 4,226,240 | A | 10/1980 | Walker, Jr. |
| 4,292,960 | A | 10/1981 | Paglione |
| 4,428,374 | A | 1/1984 | Auburn |
| 4,428,379 | A | 1/1984 | Robbins et al. |
| 4,509,528 | A | 4/1985 | Sahota |

(Continued)

FOREIGN PATENT DOCUMENTS

DE    195 28 440 A    2/1997

(Continued)

OTHER PUBLICATIONS

International Preliminary Report of Patentability for Serial No. PCT/US04/01935, mailed Jul. 8, 2005.

(Continued)

*Primary Examiner*—Anhtuan T Nguyen
*Assistant Examiner*—Elizabeth Houston

(57) ABSTRACT

An occluding device is disclosed for occluding a female patient's uterine arteries which have unsymmetrical anatomy with respect to the patient's uterine cervix. The occluding device has a pair of pivotally connected occluding members, with at least one of the occluding member having a movable occluding element on a distal shaft section of the occluding member. The position and orientation of the occluding elements on the distal shaft sections may be adjusted by operative members on the proximal shaft sections of the occluding members to accommodate for asymmetrical uterine artery anatomy. The occluding elements have pressure applying surfaces with one or more blood flow sensors such as Doppler chips which help the physician to better identify the uterine artery and to monitor blood flow therein. A tenaculum-like guiding element configured to be secured within the patient's uterine cervix, may be provided to guide the occluding device to the patient's cervix.

29 Claims, 8 Drawing Sheets

U.S. PATENT DOCUMENTS

| | | | |
|---|---|---|---|
| 4,650,466 A | 3/1987 | Luther | |
| 4,757,823 A | 7/1988 | Hofmeister et al. | |
| 4,944,741 A * | 7/1990 | Hasson | 606/206 |
| 4,945,896 A | 8/1990 | Gade | |
| 4,991,588 A | 2/1991 | Pflueger et al. | |
| 4,994,069 A | 2/1991 | Ritchart et al. | |
| 5,037,430 A | 8/1991 | Hasson | |
| 5,037,433 A | 8/1991 | Wilk et al. | |
| 5,081,997 A | 1/1992 | Bosley, Jr. et al. | |
| 5,108,408 A | 4/1992 | Lally | |
| 5,201,314 A | 4/1993 | Bosley et al. | |
| 5,226,911 A | 7/1993 | Chee et al. | |
| 5,261,409 A | 11/1993 | Dardel | |
| 5,275,166 A | 1/1994 | Vaitenkunas et al. | |
| 5,289,831 A | 3/1994 | Bosley | |
| 5,336,229 A | 8/1994 | Noda | |
| 5,336,231 A | 8/1994 | Adair | |
| 5,383,922 A | 1/1995 | Zipes et al. | |
| 5,427,108 A | 6/1995 | Bollinger | |
| 5,456,693 A | 10/1995 | Conston et al. | |
| 5,458,596 A | 10/1995 | Lax et al. | |
| 5,488,958 A | 2/1996 | Topel et al. | |
| 5,496,331 A | 3/1996 | Xu et al. | |
| 5,507,744 A | 4/1996 | Tay et al. | |
| 5,512,037 A * | 4/1996 | Russell et al. | 600/206 |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,562,680 A | 10/1996 | Hasson | |
| 5,570,692 A | 11/1996 | Morinaga | |
| 5,582,617 A | 12/1996 | Klieman et al. | |
| 5,588,960 A | 12/1996 | Edwards et al. | |
| 5,591,173 A * | 1/1997 | Schifano | 606/120 |
| 5,598,841 A | 2/1997 | Taniji et al. | |
| 5,614,204 A | 3/1997 | Cochrum | |
| 5,658,299 A | 8/1997 | Hart | |
| 5,662,676 A | 9/1997 | Koninckx | |
| 5,662,680 A | 9/1997 | Desai | |
| 5,665,096 A | 9/1997 | Yoon | |
| 5,672,153 A | 9/1997 | Lax et al. | |
| 5,672,172 A | 9/1997 | Zupkas | |
| 5,674,243 A | 10/1997 | Hale | |
| 5,691,314 A | 11/1997 | Hodgen | |
| 5,697,937 A | 12/1997 | Toma | |
| 5,697,942 A | 12/1997 | Palti | |
| 5,702,407 A | 12/1997 | Kaji | |
| 5,713,371 A | 2/1998 | Sherman et al. | |
| 5,713,896 A | 2/1998 | Nardella | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,749,879 A | 5/1998 | Middleman et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,895,395 A | 4/1999 | Yeung | |
| 5,899,861 A | 5/1999 | Friemel et al. | |
| 5,904,651 A | 5/1999 | Swanson et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,922,008 A | 7/1999 | Gimpelson | |
| 5,941,889 A | 8/1999 | Cermak | |
| 5,979,453 A | 11/1999 | Savage et al. | |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,039,693 A | 3/2000 | Seward et al. | |
| 6,045,508 A * | 4/2000 | Hossack et al. | 600/447 |
| 6,066,139 A | 5/2000 | Ryan et al. | |
| 6,077,257 A | 6/2000 | Edwards et al. | |
| 6,080,118 A | 6/2000 | Blythe | |
| 6,096,051 A | 8/2000 | Kortenbach et al. | |
| 6,106,473 A | 8/2000 | Violante et al. | |
| 6,152,874 A | 11/2000 | Looney et al. | |
| 6,169,914 B1 | 1/2001 | Hovland et al. | |
| 6,175,751 B1 | 1/2001 | Maizes | |
| 6,186,947 B1 | 2/2001 | Ouchi | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,293,954 B1 * | 9/2001 | Fogarty et al. | 606/151 |
| 6,299,621 B1 | 10/2001 | Fogarty et al. | |
| 6,368,340 B2 * | 4/2002 | Malecki et al. | 606/204 |
| 6,371,973 B1 | 4/2002 | Tepper | |
| 6,425,867 B1 | 7/2002 | Vaezy et al. | |
| 6,582,451 B1 * | 6/2003 | Marucci et al. | 606/207 |
| 6,602,251 B2 | 8/2003 | Burbank et al. | |
| 6,610,074 B2 * | 8/2003 | Santilli | 606/158 |
| 6,656,205 B1 * | 12/2003 | Manhes | 606/205 |
| 6,716,218 B2 * | 4/2004 | Holmes et al. | 606/105 |
| 6,889,116 B2 * | 5/2005 | Jinno | 700/245 |
| 6,905,506 B2 | 6/2005 | Burbank et al. | |
| 2002/0111537 A1 | 8/2002 | Taylor et al. | |
| 2002/0165579 A1 | 11/2002 | Burbank et al. | |
| 2002/0183771 A1 | 12/2002 | Altieri et al. | |
| 2002/0188306 A1 | 12/2002 | Burbank et al. | |
| 2003/0018270 A1 | 1/2003 | Makin et al. | |
| 2003/0120306 A1 | 6/2003 | Burbank et al. | |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 | 1/1997 |
| GB | 2 302 025 A | 1/1997 |
| GB | 2 311 468 A | 1/1997 |
| SU | 1 072 859 A | 2/1984 |
| WO | WO 95/02370 | 1/1995 |
| WO | WO 95/02371 | 1/1995 |
| WO | WO 96/05776 | 2/1996 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |

| | | |
|---|---|---|
| WO | WO 02/078521 | 10/2002 |

OTHER PUBLICATIONS

International Search Report for PCT/US2004/038111, mailed May 3, 2005.
Written Opinion for PCT/US2004/038111, mailed May 3, 2005.
Translation of FR 1 220 773.
International Search Report for PCT/US2004/038276, mailed Mar. 15, 2005.
International Search Report for PCT/US04/01935 mailed Feb. 15, 2005.
International Search Report for PCT/US04/03023 mailed Feb. 9, 2005.
International Search Report for PCT/US03/35815 mailed Jun. 30, 2004.
Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.
Bateman, William M.D., "Treatment of intractable menorrhagia by bilateral uterine vessel, Interruption", *Am. J. Obst. & Gynec.* 89(6):825-827 (Jul. 15, 1964).
Brigato, G. et al., "A Noninvasive Instrumental Method in Severe Postpartum Hemorrhages", *Minerva Ginecologica* 50(7-8):337-339 (1998).
Brohim, Robert M. et al., "Development of Independent Vessel Security After Ligation With Absorbable Sutures or Clips", *The American Journal of Surgery*, Mar. 1993, vol. 165, pp. 345-348.
Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.
Fuchs, Karl, "Afibrinogenemia Treated by Ligation of Uterine Arteries", *Gynacologic* 148:407-411(1959).
Garza Leal, J. et al., "Myoma Treatment by Transient Uterine Ischemia", *The Journal of the American Association of Gynecologic Laparoscopists* 7(3):S31 (Aug. 2000).
Hay, D.L. et al., "Hemostasis in Blood Vessels After Ligation", *Am. J. Obstet. Gynecol.*, Mar. 1989, 160:3, pp. 737-739.
Hunerbein, M. et al., "Endoscopic Ultrasound-Guided Real Time Biopsy of Peri-Intestinal Tumors", *Surgical Technology International VII*, 1998, pp. 91-95.
O'Leary, James A., M.D., "Uterine Artery Ligation in the Control of Postcesarean Hemorrhage", *The Journal of Reproductive Medicine, Inc.*, 40(3):189-193 (Mar. 1995).
O'Leary, James L., M.D. et al., "Uterine artery ligation in the control of intractable postpartum hemorrhage", Am. J. Obst. & Gynec. 94(7):920-924 (Apr. 1, 1966).
Ravina, J.H. et al., "Arterial Embolisation to Treat Uterine Myomata", *The Lancet*, Sep. 9, 1995, vol. 346, No. 8976, pp. 671-672.
Schaefer, C.J. et al., "Absorbable Ligating Clips", *Surg. Gynecol. Obstet.*, 1982, 154:513-516.
"Mick 200-TP Applicator Package", Mick Radio-Nuclear Instruments, Inc., advertisement.
"Multiplanar Biopsy Transverse Scan", Bruel & Kjaer Medical Systems, Inc., advertisement.
"Seeding Device—Proscan Urologic Ultrasound Imaging System", Teknar, advertisement.
Sonopsy Ultrasound Guided Breast Biopsy, NeoVision, advertisement.
"Transrectal Biopsy of the Prostrate Gland", Bruel & Kjaer Medical Systems, Inc., advertisement.

* cited by examiner

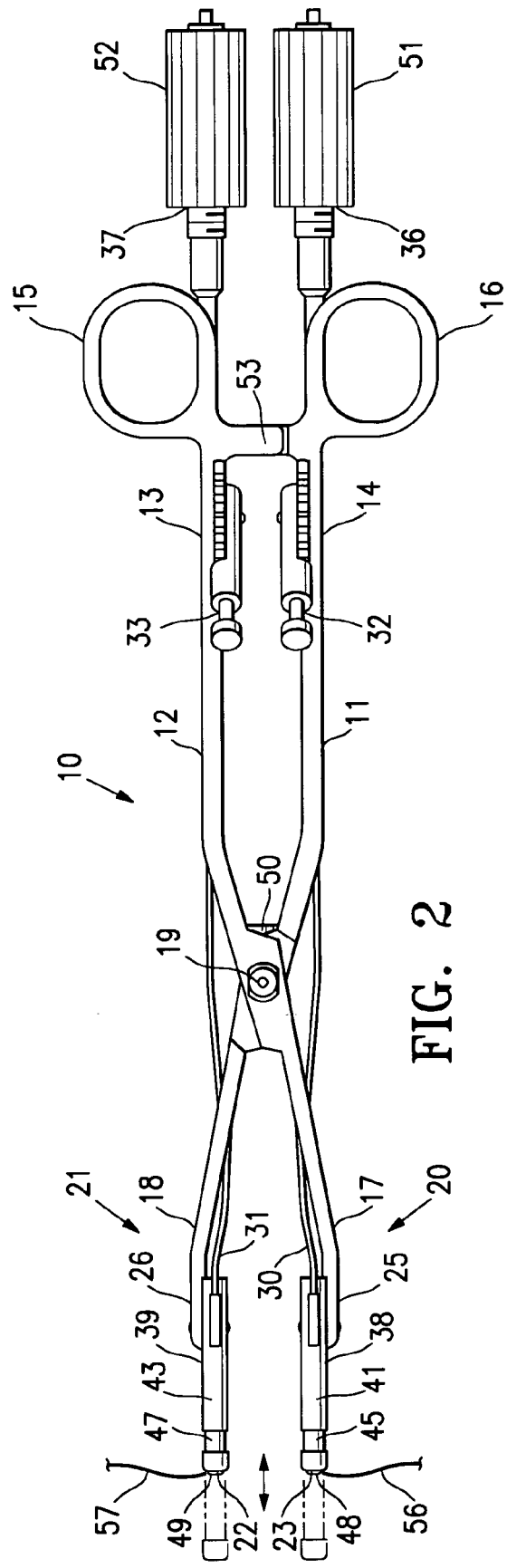
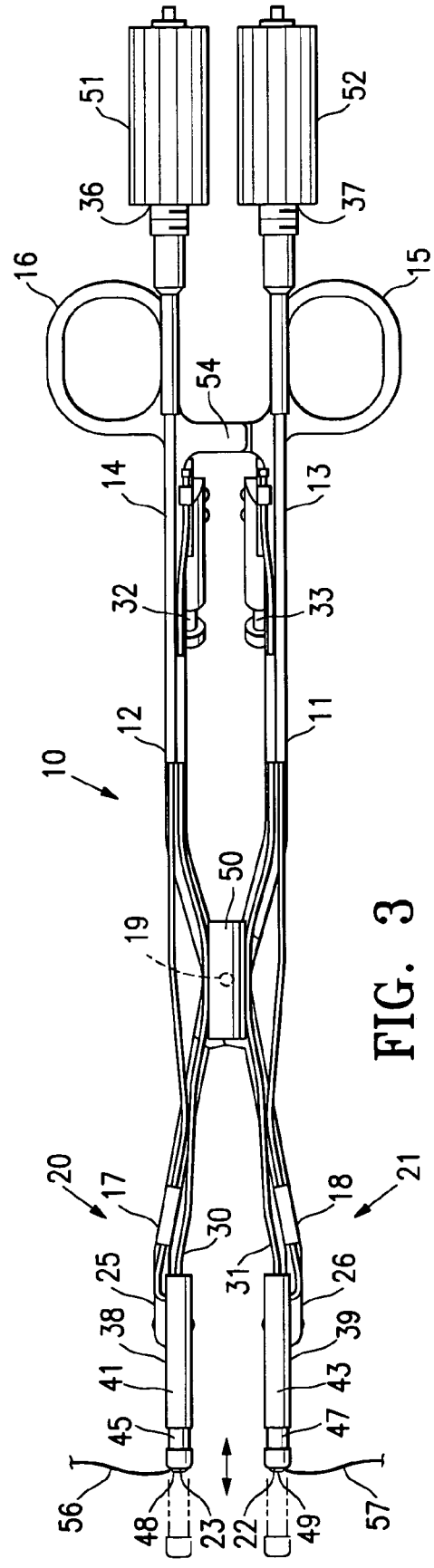

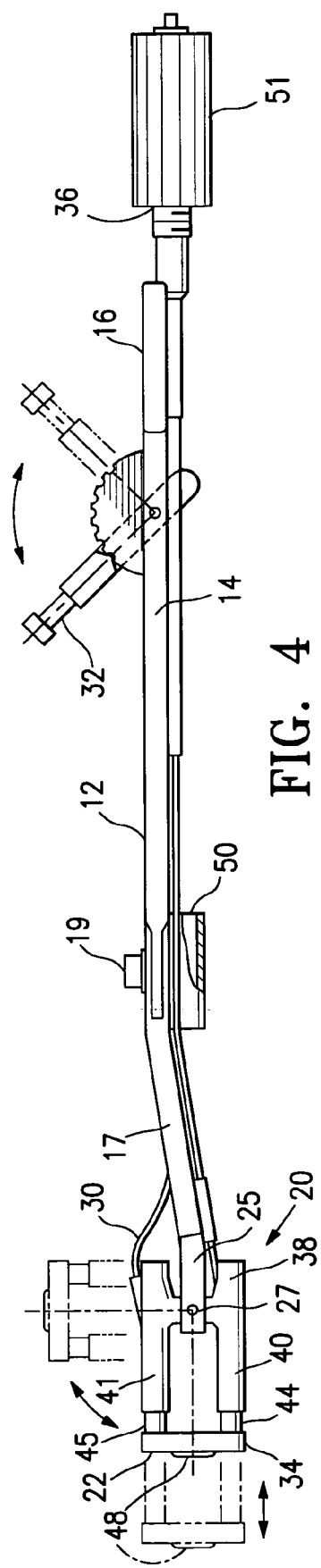
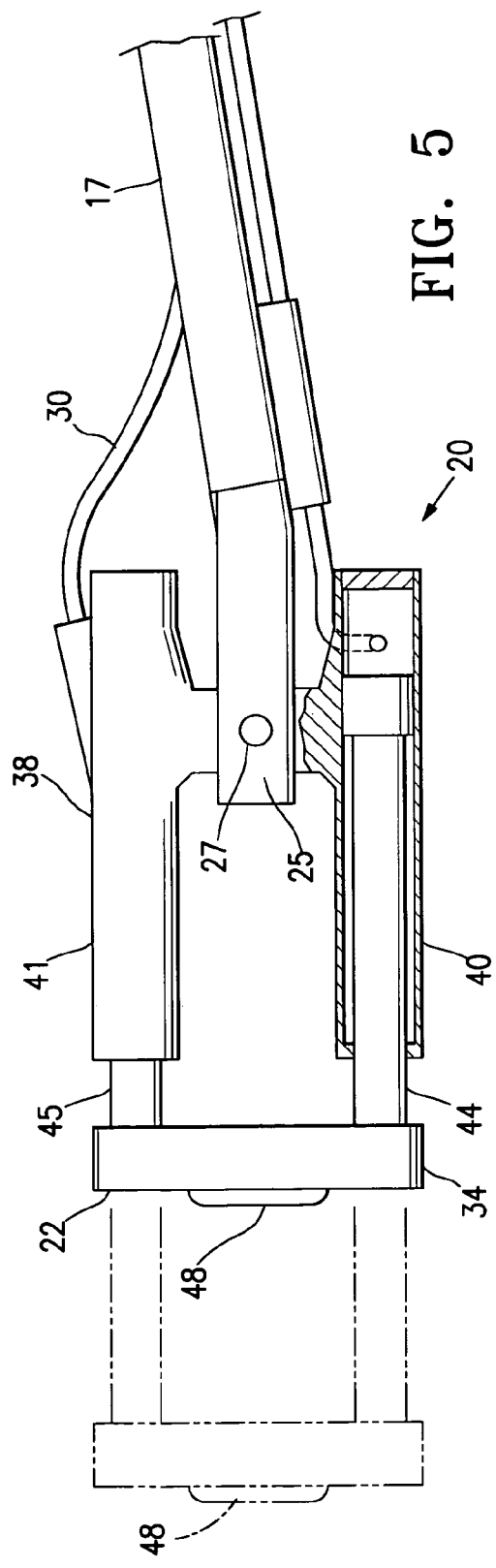
FIG. 4
FIG. 5

OCCLUSION DEVICE FOR ASYMMETRICAL UTERINE ARTERY ANATOMY

FIELD OF THE INVENTION

The invention is generally directed to the treatment of uterine disorders by detecting and regulating blood flow through one or both of the patient's uterine arteries.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Thus, any method which can approximate the therapeutic result of a hysterectomy without removing the uterus would be a significant improvement in this field. Newer treatment methods have been developed for some diseases which may spare these women a hysterectomy.

In an article published in 1964, Bateman reported that uterine artery vessel ligation or division. achieved via infra-abdominal surgery similar to hysterectomy, was effective in treating menorrhagia both with and without myomectomy. Bateman, W., M. D., "Treatment of intractable menorrhagia by bilateral uterine vessel interruption", 89 Am. J. Obstet. Gynecol. 825-827 (Harcourt Health Sciences, Jul. 15, 1964). While Bateman reported some success, this procedure involves opening the abdominal cavity, with the known attendant risks and disadvantages.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is known as "uterine artery embolization". In this technique, uterine arteries are accessed via a transvascular route from a common femoral artery into the left and right uterine arteries by means of an intravascular catheter and embolic material, such as small metallic coils, polyvinyl alcohol particulate and the like, is delivered through the catheter to the uterine arteries which quickly become occluded.

See also Burbank, Fred, M. D., et al, Uterine Artery Occlusion by Embolization or Surgery for the Treatment of Fibroids: A Unifying Hypothesis Transient Uterine Ischemia, The Journal of the American Association of Gynecologic Laparoscopists, November 2000, Vol. 7, No. 4 Supplement, pp. S3-S49. U.S. Pat. No. 6,254,601, to Fred Burbank et al, entitled "Methods for Occlusion of the Uterine Arteries", describes numerous devices and methods useful for occluding a uterine artery by penetrating the tissue of the patient to access the uterine artery. The devices and methods described in Burbank '601 have been useful in occluding a uterine artery, however there have been some difficulties encountered with their use.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al. and Burbank et al., the ischemic effects on the fibroid is greater than the effect on the uterus. In most instances, the fibroid withers and ceases to cause clinical symptoms.

However, many physicians do not possess the training or equipment necessary to perform catheter-based uterine artery embolization under radiologic direction. Accordingly, there are substantially fewer uterine artery embolizations performed, worldwide, each year than hysterectomies for symptomatic uterine fibroids.

Recently, fibroid treatment procedures have been described wherein the uterine arteries are temporarily occluded by an intravaginal device which is non-invasively pressed against the patient's vaginal fornix and clamped or otherwise pressed against tissue bundle with the patient's uterine artery being within the bundle. Pressure on the tissue occludes the underlying uterine artery. While these procedures have shown much promise, they are not always successful with many female patients who have asymmetrical uterine artery anatomy.

What is needed, therefore, are intravaginal devices and procedures for using such devices to occlude blood flow in a female patient's uterine arteries that can be easily used by physicians with limited training and equipment with patient's having asymmetrical uterine artery anatomy.

SUMMARY OF THE INVENTION

The invention is directed to a relatively non-invasive intravaginal uterine artery occlusion device and the procedure for using the device and system for treating a female patient's uterine disorder by occluding one or both of the patient's uterine artery. The devices and their use may be utilized in the treatment of uterine fibroids, dysfunctional uterine bleeding (DUB), post partum hemorrhage (PPH) and other uterine disorders by reducing or terminating blood flow through a patient's uterine artery. The invention is particularly useful for occluding asymmetrical uterine arteries.

An occlusion device embodying features of the invention has at least one and preferably a pair of occluding members with adjustable pressure applying surfaces. The occluding members have an elongated shaft with a proximal shaft section which is configured in part to extend out of the patient during the procedure and a distal shaft section which has occluding elements on the distal shaft section with pressure applying surfaces for artery occlusion. The occluding elements which are movable with respect to the distal shaft sections to adjust the relative position of the pressure applying surfaces for improved uterine artery occlusions with a female patient's asymmetrical uterine anatomy. Movement of the occluding elements is controlled by operative elements on the proximal shaft section which are configured to extend out of the patient during the occlusion procedure.

The occluding elements may be configured for movement along the longitudinal axis of the distal shaft section of the occluding member, for rotation about a pivot point on or adjacent to the distal shaft section, for radial movement away from the longitudinal axis of the distal shaft section, rotational movement about the longitudinal axis of the distal shaft section or a combination of such movements to accommodate a particular uterine anatomy.

The movement of the occluding elements may be effected by a fluid pressure actuated device, a suitable mechanism such as a screw actuated mechanism electromechanical systems and other suitable systems.

The elongated shafts of the occluding members are preferably pivotally mounted so that movement of the proximal shaft sections of the occluding members. which extend out of the patient during the procedure, will adjust the spacing between the distal shaft sections and as a result, the pressure applying surfaces of the occluding elements on the distal shaft sections.

The pressure applying surfaces of the occluding elements are configured to apply pressure against the patient's uterine cervix or against the patient's vaginal fornix or both to occlude underlying uterine arteries. Adjustment of the occluding element position is employed to optimize the orientation of the pressure applying surfaces thereof to effectively press against the patient's uterine cervix and/or vaginal fornix to occlude the patient's underlying uterine arteries in a variety of different anatomical structures.

The occlusion device should be stabilized with respect to the patient's uterus by a positioning member such as a tenaculum to facilitate a more effective application of pressure by the pressure applying member to the exterior of the cervix or the vaginal fornix to ensure occlusion of the patient's uterine artery.

In one embodiment of the invention, the occluding members are provided with blood flow sensors to aid in the location of the patient's uterine arteries, and to monitor the occlusion thereof. When the pressure applying surfaces of the occluding elements are pressed against the wall of the vaginal fornix, the vaginal wall is distended so as to more closely approach a uterine artery. Applying tension to the uterine cervix by the tenaculum or other suitable device or implement, including forceps, suction devices, and the like, help to reduce the distance from the patient's vaginal fornix to the patient's uterine artery.

The blood flow sensors on the occluding elements may sense sound, pressure, strain, stress, chemical entity, electromagnetic radiation and the like, and may be a combination of such sensors. A preferred blood flow sensor is one based on Doppler ultrasound. The blood flow sensor is preferably mounted to the face of a tissue-contacting, pressure applying surface of the occluding element and is preferably oriented perpendicularly to the pressure applying surface. Other orientations may be employed. Ultrasound energy useful for sensing a location of a blood vessel or of blood flow in a blood vessel has a frequency of less than about 20 MegaHertz (MHz), such as between about 5 MHz and about 19 MHz, and preferably between about 6 MHz and about 10 MHz. In commercially available Doppler sensors, the frequency is typically about 8 MHz. For sensors based on electromagnetic energy useful for sensing a location of a blood vessel or of blood flow in a blood vessel, the EM energy should have a wavelength of about 500 nanometers (nm) to about 2000 nm, preferably about 700 nm to about 1000 nm.

A method for occluding a patient's uterine arteries which embodies features of the invention includes advancing the occluding device through the patient's vaginal canal, preferably slidably mounted on a previously deployed tenaculum or tenaculum-like device. The stabilizing bar of the tenaculum, which is deployed within the patient's uterine cervix, guides the occluding device so that the occluding elements of the device are disposed adjacent to the patient's cervix. The position of the occluding elements on the occluding device is adjustable so that the pressure applying surfaces of the occluding elements may be pressed against the patient's vaginal fornix on both sides of the cervix. The position of the occluding elements is adjusted utilizing the blood flow sensors on the pressure applying surfaces of the occluding elements to ensure the pressure applying surfaces are properly positioned with respect to the uterine arteries for effective occlusion thereof. Positional adjustment of the occluding elements may be in-line with the distal shaft sections, rotation within a plane in line with the distal shaft section, radial extension away from distal shaft section, rotation about the longitudinal axis and combinations of these movements. Pressure is applied to the uterine arteries by the occluding elements to occlude the arteries for a period of about 0.5 to about 48 hours, usually about 1 to about 24 hours for effective treatment of the uterine disorder.

The invention allows for the non-surgical location and occlusion of blood vessels such as the uterine artery, providing effective therapeutic treatment. Importantly, the present invention allows for the occlusion of a female patient's uterine artery without the need for radiographic equipment or for extensive training in the use of radiographic techniques. The devices and methods are simple and readily used for treating uterine fibroids, dysfunctional uterine bleeding (DUB), adenomyosis, post-partum hemorrhage, and other uterine disorders. The devices, systems and methods embodying features of the invention allow for the occlusion of both uterine arteries in those situations in which the uterine anatomy is not symmetrical.

These and other advantages will become more apparent from the following detailed description when taken in conjunction with the accompanying exemplary drawings.

BRIEF DESCRIPTION OF THE DRAWINGS

FIG. 2 is a top view of the uterine artery occluding device shown in FIG. 1.

FIG. 3 is an bottom view of the uterine artery occluding device shown in FIG. 1.

FIG. 4 is an elevational view of the occluding device shown in FIG. 1.

FIG. 5 is an enlarged view of the distal portion of the uterine artery occluding device shown in FIG. 4.

DETAILED DESCRIPTION OF THE INVENTION

Figure 1:
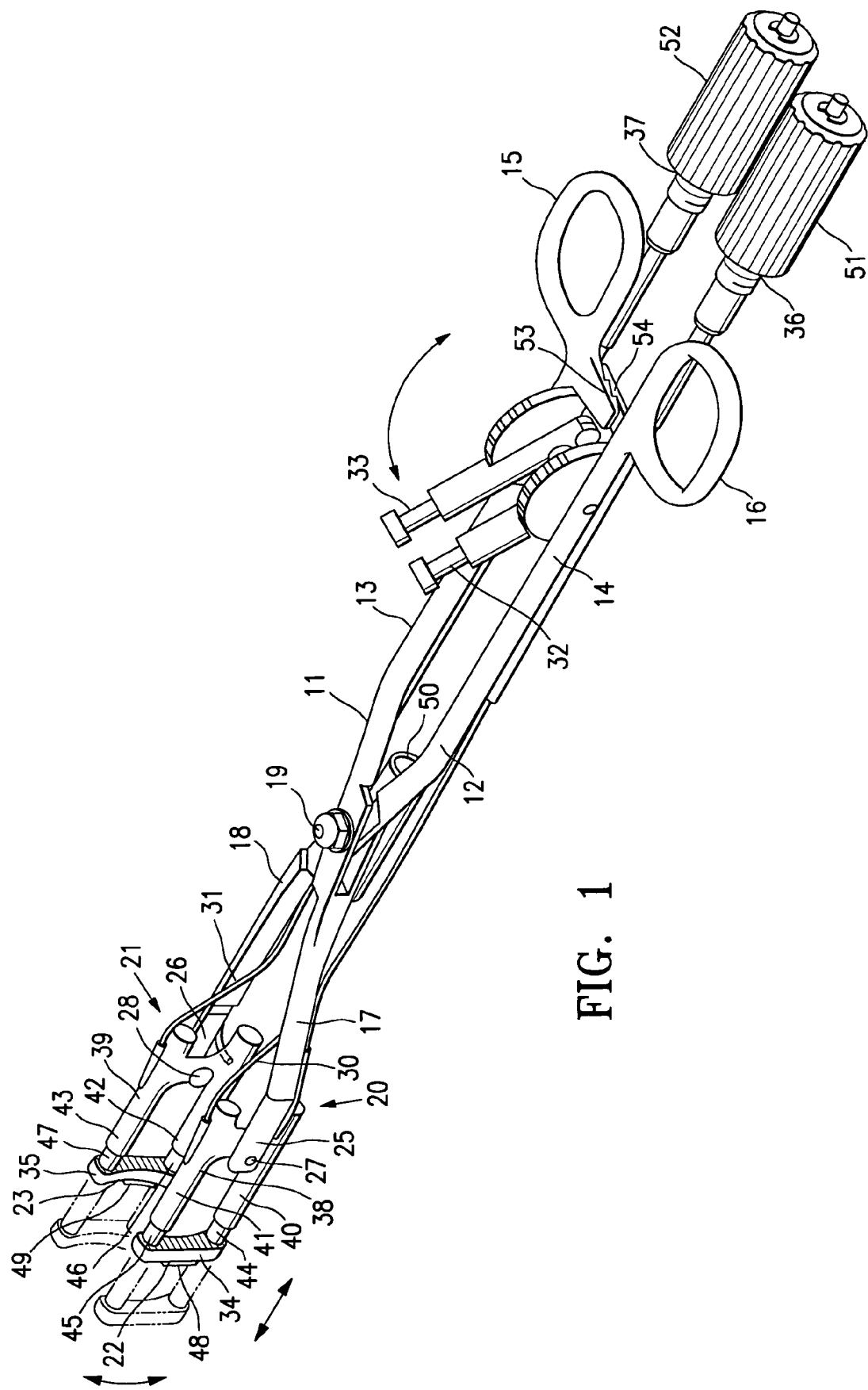
FIG. 1 is a perspective view of a uterine artery occluding device which embodies features of the invention.
Figure 6:
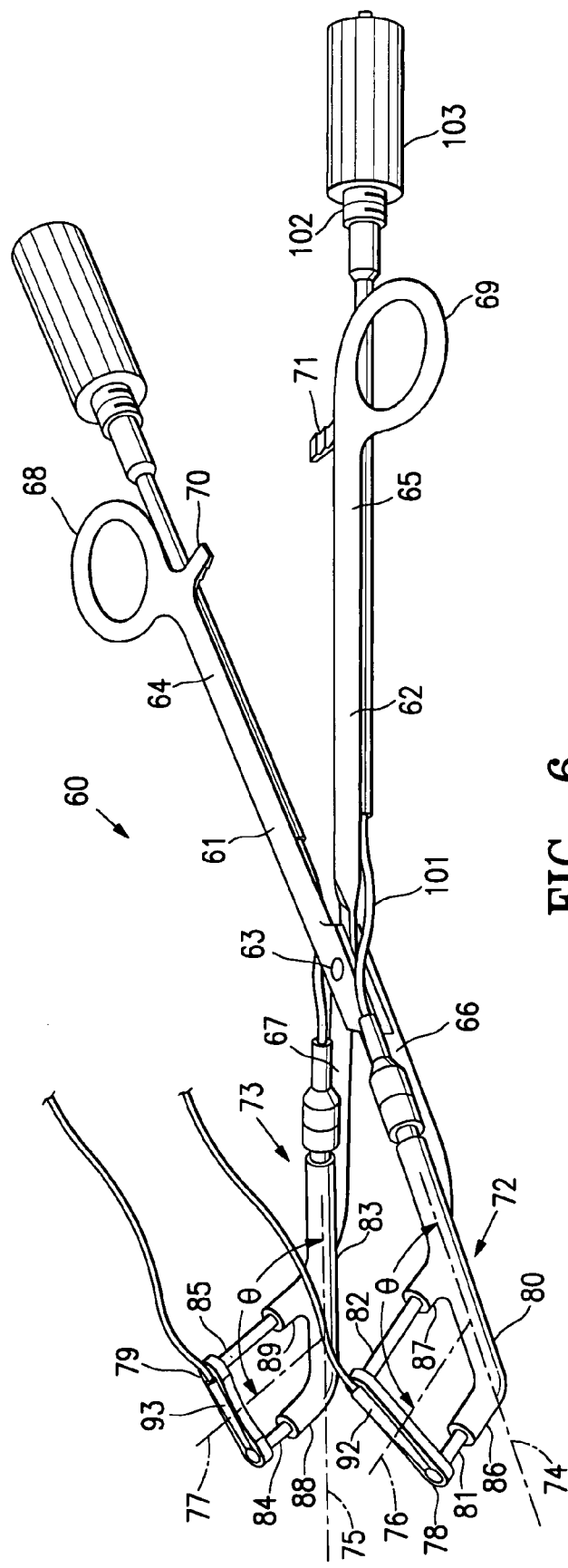
FIG. 6 is a perspective view of an alternative occluding device embodying features of the invention.
Figures 7, 8:
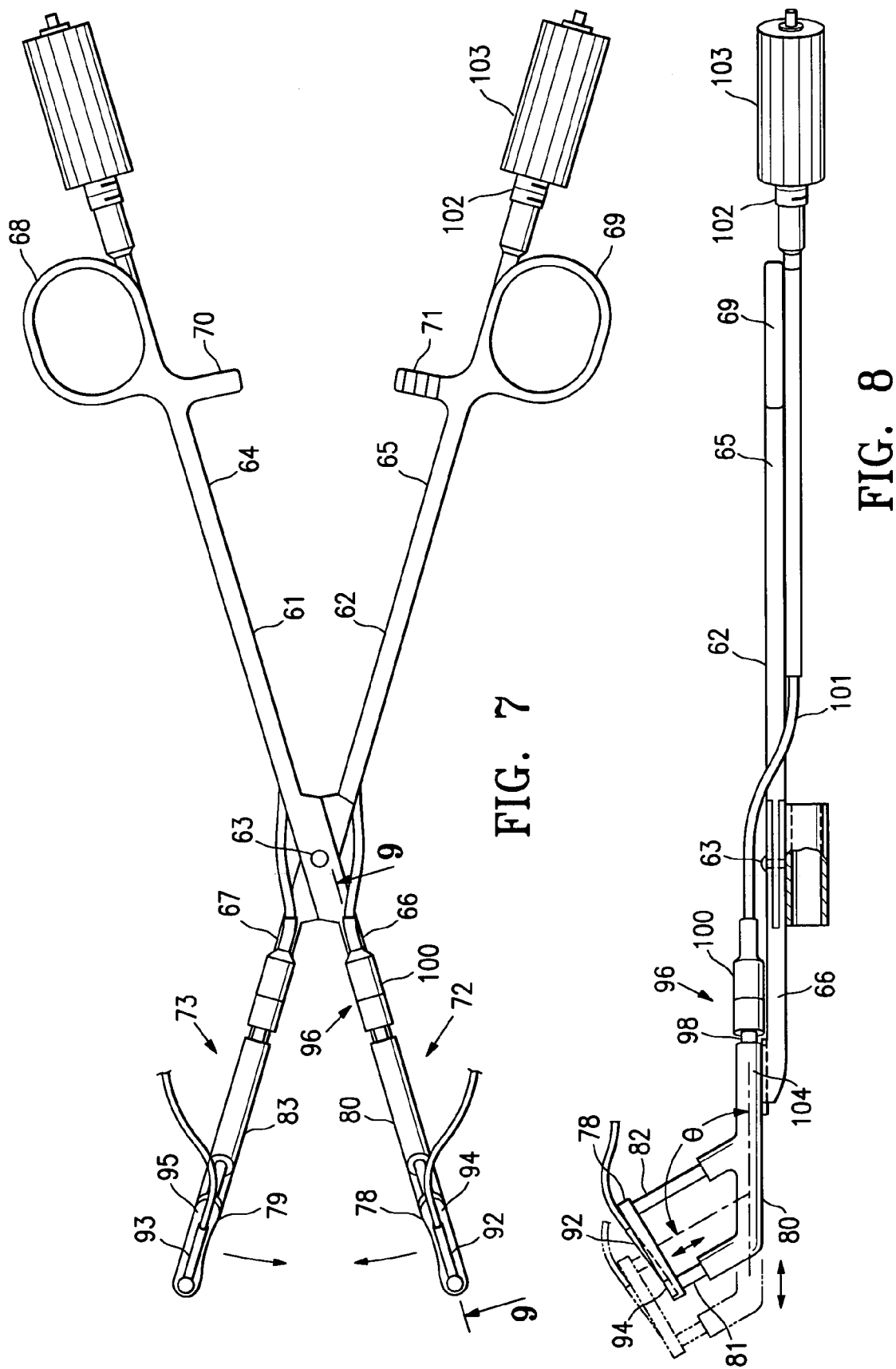
FIG. 7 is top view of the occluding device shown in FIG. 6.
FIG. 8 is an elevational view, partially in section, of the occluding device shown in FIG. 7.

FIGS. 1-6 illustrate a relatively non-invasive intra-vaginal occluding device 10 embodying features of the invention. The device 10 includes a pair of elongated occluding members 11 and 12, each of which has a proximal shaft section 13 and 14 respectively with finger grips 15 and 16, and distal shaft sections 17 and 18 with occluding elements 20 and 21 having pressure-applying surfaces 22 and 23 respectively. The elongated occluding members 11 and 12 are pivotally connected at pivot point 19.

The occluding elements 20 and 21 on the distal portion of the distal shaft sections 17 and 18 are shown pivotally mounted to the distal ends 25 and 26 of the distal shaft sections 17 and 18 respectively at pivots 27 and 28. The occluding elements 20 and 21 are rotated about the pivotal connections 27 and 28 by control cables 30 and 31 which are connected to control arms 32 and 33 respectively mounted on the proximal shaft sections 14 and 13. The control arms 32 and 33 are provided with a ratchet mechanism (not shown) to hold the control arms, and thus the occlusion elements 20 and 21 in a selected position. The pressure applying occluding bars 34 and 35 of the occluding elements 20 and 21 may be axially extended by hydraulic systems 36 and 37 as depicted in FIG. 5.

The occluding elements 20 and 21 are formed of yokes 38 and 39 with arms 40 and 41 and arms 42 and 43 respectively which are configured to slidably receive the legs 44 and 45 depending from occluding bar 34 and legs 46 and 47 depending from occluding bar 35. Blood flow sensors 48 and 49 are secured to the pressure applying surfaces 22 and 23.

The occlusion device 10 is advanced within the patient's vaginal canal with the occlusion elements 20 and 21 in a straight, forward position until the occlusion elements reach the patient's uterine cervix. The shoe 50 on the device 10 preferably slides along the positioning rod of a previously positioned tenaculum (not shown) to ensure that the occluding elements 20 and 21 are positioned on opposite sides of the patient's uterine cervix. The control cables 30 and 31 are pulled by the control arms 32 and 33 to rotate the occlusion elements 20 and 21 into position with the pressure applying surfaces 22 and 23 are oriented transverse to the patient's uterine arteries. The knobs 51 and 52 of the hydraulic mechanisms 36 and 37 are rotated clockwise to compress the fluid within the hydraulic systems to advance the legs 44 and 45 within the arms 40 and 41 and legs 46 and 47 within the arms 42 and 43 so the occlusion bars 34 and 35 connected to the legs advance against the patient's vaginal fornix to occlude the patient's uterine arteries. The blood flow sensors 48 and 49 on the occluding elements 20 and 21 help the physician to properly position the pressure applying surfaces 22 and 23 of the occluding elements for effective artery occlusion. The physician may then squeeze the finger grips 15 and 16, to adjust the spacing between the occluding elements 20 and 21 to occlude the underlying uterine arteries. The ratchet locking members 53 and 54 on the proximal shaft sections 13 and 14 which interact to releasably lock the occluding members 11 and 12 together when the finger grips 15 and 16 are squeezed. Upon completion of the procedure, the ratchet locking members 53 and 54 may be released and the occluding device 10 removed from the patient's vaginal canal.

The blood flow sensors 48 and 49 are preferably Doppler ultrasonic sensing systems to allows the operator to more easily guide the occlusion members 11 and 12 to the location of the patient's target uterine arteries. Sensors 48 and 49 are provided with a signal transmission cables 56 and 57 which are operatively connected to sensor control device (not shown). Cables 56 and 57 may be insulated wires, a plurality of wires, optical fibers, waveguides, or other connection effective to carry signals and/or energy or power between the sensors and a sensor controller.

Suitable Doppler ultrasonic systems include the MedaSonics® CardioBeat® Blood Flow Doppler with Integrated Speaker (Cooper Surgical, Inc., Trumbull, Conn.). Other commercially available suitable Doppler ultrasound sensors are the Koven model ES 100X MiniDop VRP-8 probe (St. Louis, Mo.) and the DWL/Neuro Scan Medical Systems' Multi-Dop B+ system (Sterling, Va.).

While not shown in the drawings, the pressure applying surface of the occluding elements may be provided with a serrated or other tissue-grasping surface which is configured to engage and hold onto tissue when the pressure applying surfaces are pressed into tissue of the patient's vaginal fornix.

FIGS. 6-9 illustrate an alternative occluding device 60 embodying features of the invention comprising occluding members 61 and 62 which are pivotally connected at pivot 63. The occluding members 61 and 62 have proximal shaft sections 64 and 65 and distal shaft sections 66 and 67. The proximal shaft sections 64 and 65 include finger grips 68 and 69 and ratchet locking members 70 and 71. The distal shaft sections 66 and 67 have occluding elements 72 and 73 which are inclined at angle θ with respect to the longitudinal axis 74 and 75 of the distal shaft sections 66 and 67 (measured from a line 76 and 77 perpendicular to the occlusion bars 78 and 79. The angle θ can range from about 90° to about 190°, preferably about 135° to about 170°. The angulation of the occluding elements 72 and 73 provides a more direct attack angle on the patient's uterine arteries to facilitate directing the pressure applying surfaces toward a desired location at the patient's vaginal fornix to facilitate location and occlusion of the patient's uterine artery. The ratchet locking members 70 and 71 are preferably releasable so that occluding members 61 and 62 of clamping device 60 can be released after the limited treatment time to re-establish blood flow to the uterine tissue.

Figure 9:
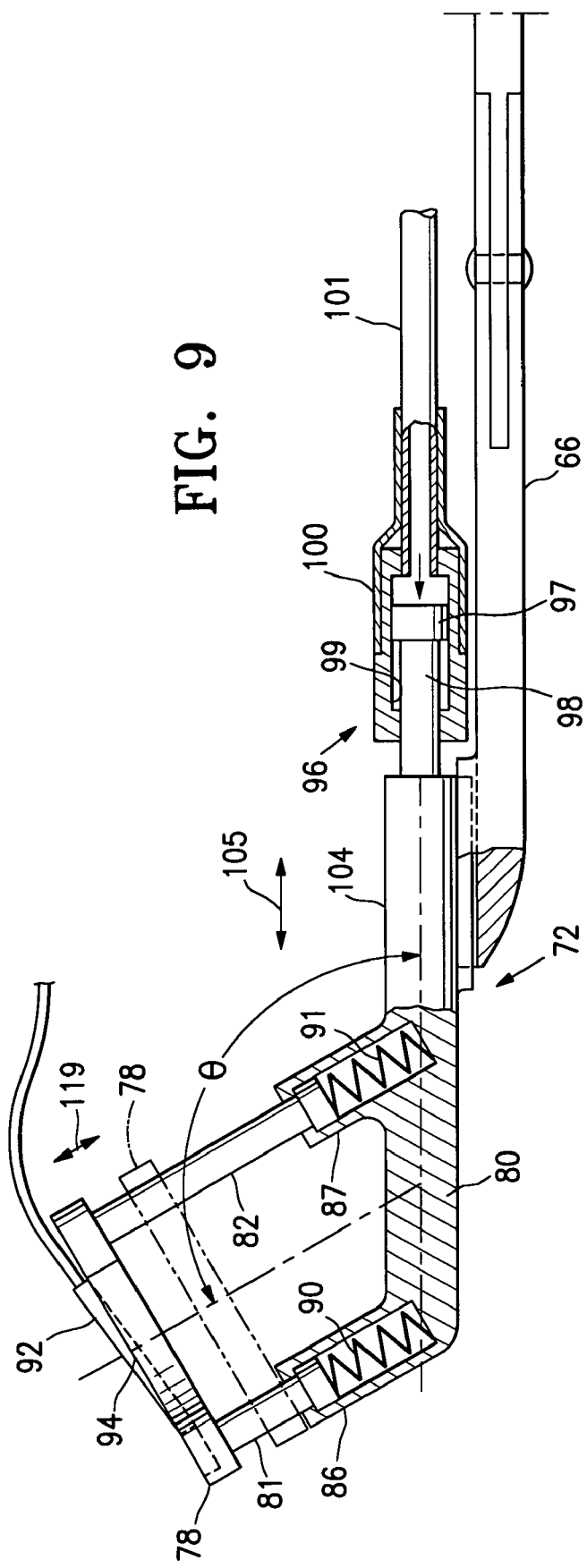
FIG. 9 is an enlarged elevational view, partially in section, of the distal portion of the device shown in FIG. 8.

The occluding elements 72 and 73 have yoke member 80 which receives legs 81 and 82 and yoke member 83 which receives legs 84 and 85 extending from the underside of occlusion bars 78 and 79. The yoke 80 has arms 86 and 87 and yoke 83 has a pair of arms 88 and 89 which slidably receive the legs 81 and 82 and 84 and 85 of the occlusion bars 78 and 79. As shown in FIG. 9, springs 90 and 91 are provided within the arms 86 and 87 to exert a biased pressure against the legs 81 and 82 respectively to urge the occlusion bar 78 away from the distal shaft section 66 to ensure that the pressure applying occlusion bar 78 applies sufficient pressure against the patient's vaginal fornix to at least partially occlude underlying uterine arteries. The arms 88 and 89 of yoke 83 are similarly biased. Blood flow sensors 92 and 93 are positioned on the pressure applying surfaces 94 and 95 to facilitate location of uterine arteries and may be used to monitor blood through the arteries once occluded.

As shown in more detail in FIG. 9, the occluding element 72 is configured to move distally and proximally by the hydraulic system 96, including piston 97 which is secured to piston rod 98 and which is slidably disposed within the chamber 99 of housing 100. Hydraulic line 101 connects the threaded pressure applicator 102 on the proximal shaft section 65 with the inner chamber 99 in housing 100. Rotation of the knob 103 on pressure applicator 102 generates increased fluid pressure which drives the piston 97 in chamber 99 Piston rod 98 is secured to the proximal end 104 of yoke 80 so that movement of piston 97 moves the yoke 80 which is slidably secured to the distal end of the distal shaft section 66. Yoke 80 may be configured to move away and toward the distal shaft section 66 as shown by the arrow 105. The occlusion element 73 is the mirror image of the occlusion element 72 and has corresponding parts and may be moved by the same or similar mechanism or system.

The uterine arteries in human females are located adjacent the vaginal mucosa at a location within a few centimeters of the vaginal fornix. As a result, for accessing and occluding a uterine artery from within the patient's vaginal canal, the dimensions of a vagina determine what size occluding device is suitable, taking into consideration that the occluding device should readily reach the vaginal fornix and be manually operated from outside of a patient's body. For example, a occluding device may be between about 6 inch to about 12 inches (15.2-30.5 mm) in length for most applications.

Figure 10:
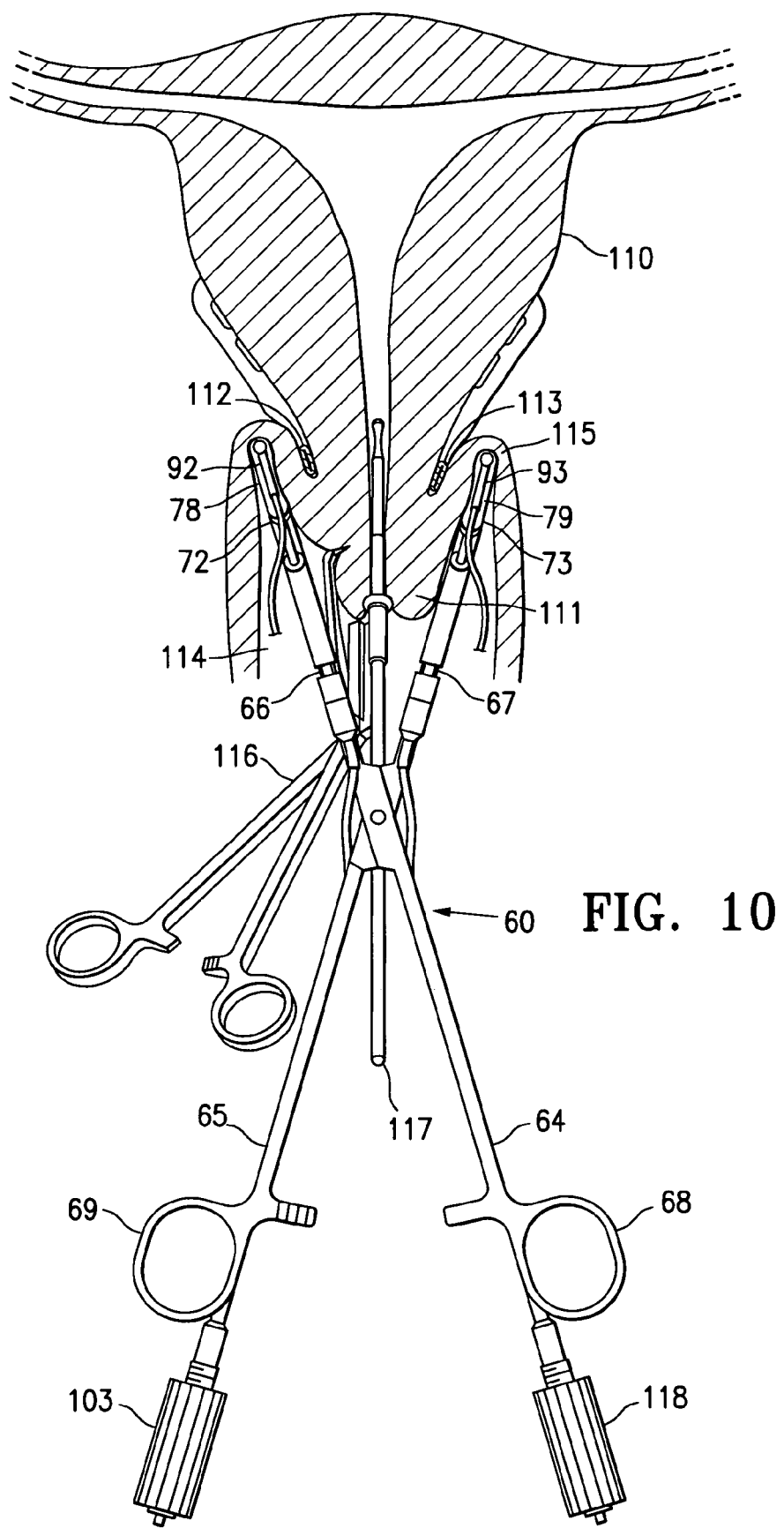
FIG. 10 schematically illustrates the placement of the occluding device shown in FIGS. 6-9 within a female patient's vaginal canal with the pressure applying surfaces of the occluding elements pressed against the patient's vaginal fornix to occlude the patient's uterine arteries.

FIG. 10 schematically illustrates the deployment of the occluding device shown in FIGS. 6-9 in a human female reproductive system. Anatomically shown are a uterus 110, uterine cervix 111, uterine arteries 112 and 113, vaginal canal 114 and vaginal fornix 115. A method of using the uterine artery occlusion device embodying features of the invention includes introducing the occlusion device 60 into the patient's vaginal canal 114 and advancing the device therein over the tenaculum 116 which has been previously positioned within the patient's vaginal canal 114 with the post 117 thereof disposed within the patient's cervix 111. The occluding device 60 is advanced over the post 117 of tenaculum 116 until the occluding elements 72 and 73 on the distal shaft sections 66 and 67 of the device 60 are positioned on opposite sides of the patient's uterine cervix 111. The position of the occluding elements 72 and 73 are adjusted by turning the knobs 103 and 118 to increase the pressure in the hydraulic system 96 to drive the legs 81-82 and 84-85 and attached occlusion bars 78 and 79 away from the yokes 80 and 83 as shown by the arrows 105 and 119. (See FIGS. 6 and 9) Once the occluding elements 72 and 73 are positioned transverse to the uterine arteries 112 and 113 the finger grips 68 and 69 on the proximal shafts are squeezed together to decrease the spacing between the occluding elements 72 and 73. With the guidance of the Doppler sensors 92 and 93, the pressure applying surfaces 94 and 95 of the occlusion bars 78 and 79 (See FIG. 6) are positioned as close as possible to the patient's uterine artery 112 and 113. Sufficient pressure is applied to the underlying uterine arteries 112 and 113 or the tissue surrounding the uterine arteries to facilitate artery occlusion. The proximal shaft sections 64 and 65 are locked by ratchet locking members 70 and 71 to press the pressure applying surfaces against the tissue of the vaginal fornix for artery occlusion. The locked position is maintained for about 0.5 to about 48 hours, preferably about 1 to about 22 hours for effective therapeutic treatment of a uterine disorder, e.g. for fibroids, PPH, DUB and the like. Blood flow sensors 92 and 93 are effective to locate uterine arteries 112 and 113 by detecting blood flow and monitoring the treatment by detecting the lack of blood flow in the arteries.

Figure 11:
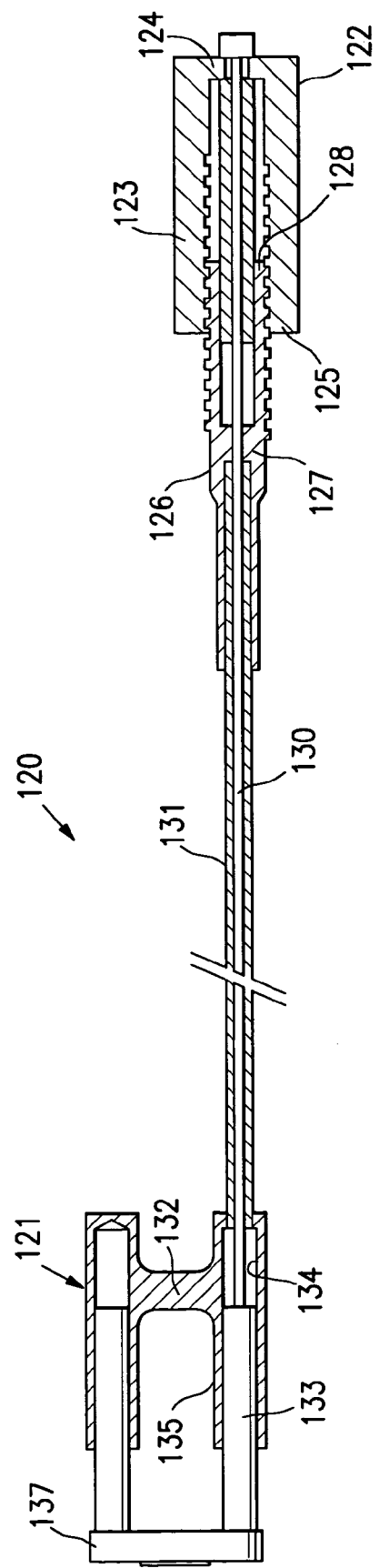
FIG. 11 illustrates an alternative mechanism for moving a pressure applying head of an occlusion device.

FIG. 11 is an elevational view in section of an alternative mechanical system 120 for manipulating the occluding element 121. The mechanical system 120 includes an operable handle 122 which has a first cylindrical member 123 with one closed end 124 and one open end 125 and a second cylindrical member 126 with one closed end 127 and one open end 128. The open ends 125 and 128 inter-fit, with the open end 125 having a threaded interior and the open end 128 having a threaded exterior. Drive shaft 130 is secured to the closed end 124 of cylindrical member 123 and is rotatable and longitudinally slidable through the closed end 127 of the second cylindrical member 126 so that rotation of one of the cylindrical members with respect to the other adjusts the distance between the closed ends 124 and 127 of the first and second cylindrical members respectively. The drive shaft 130 extends through outer tubular member 131 which is secured by its distal end to the pressure applying head 132 and by its proximal end to the closed end 127 of the second cylindrical member 126. The outer tubular member 131 is preferably a relatively flexible tube. The distal end of drive shaft 130 engages the leg 133 which is slidably disposed within the recess or bore 134 in arm 135 of pressure applying head 132. Upon contraction of the distance between the closed ends 124 and 127 of cylindrical members 123 and 126 respectively, the drive shaft 130 is driven through the outer tubular member 131 and the distal end of drive shaft 130 is urged against the leg 133 which depends from the occluding bar 137, and in turn drives the occlusion bar 137 distally. A second occluding member (not shown) may be pivotally connected to another occluding member which is pivotally connected to occluding member 121 in a manner previously described, and may be provided with essentially the same mechanical system as that described for mechanical system 120. A similar mechanic system may be utilized to rotate the pressure applying heads.

The uterine artery occluding devices embodying features of the invention may be made from any suitable material or combination of materials, including metals such as stainless steel, cobalt-chromium alloys, cobalt-chromium-nickel alloys, chromium-cobalt-molybdenum alloys and superelastic alloys such as nickel-titanium alloys having a stable austenite phase at body temperature, high strength plastics, ceramics, and other materials known in the art to be suitable for the uses contemplated herein. Biocompatible polymers such as polycarbonate, polysulfone, polyester, polyacetal and a variety of fluoropolymers can be suitable for a variety of embodiments of the invention. The occlusion devices and systems embodying features of the invention may be designed for single use (disposable) or may be sterilizable and capable of multiple use.

While particular forms of the invention have been illustrated and described, it will be apparent that various modifications can be made to the invention and that individual features shown in one embodiment can be combined with any or all the features of another embodiment described herein. For example, the mechanism shown in FIGS. 1-5 for moving the occluding element along the longitudinal axis of the distal shaft section of the occluding member, may be utilized in the embodiment shown in FIGS. 6-9. Accordingly, the invention is not to be limited to the specific embodiments illustrated and should be defined by the scope of the appended claims as broadly as the prior art will permit. Terms such as "element", "member", "device", "sections", "portion", "section", "steps", "means" and words of similar import, if used in the appended claims, shall not be construed as invoking the provisions of 35 U.S.C. §112(6) unless the claims expressly use the term "means" followed by a particular function without reciting specific structure or use the term "step" followed by a particular function without reciting specific action.

What is claimed is:

1. An intravaginal device for occluding a female patient's uterine arteries with an unsymmetrical anatomy to treat a uterine disorder, comprising:

a. a first occluding member having a first elongated shaft, a first operative proximal shaft section configured to extend out of the patient during treatment, a first distal shaft section with a first pressure applying occluding element secured to the first distal shaft section, and a first mechanism to distally extend at least part of the first pressure applying occluding element from a first position closer to the first operative proximal shaft section to a second position further away from the first operative proximal shaft section; and b. a second occluding member having a second elongated shaft, a second operative proximal shaft section configured to extend out of the patient during treatment and a second distal shaft section with a second pressure applying occluding element secured to the second distal shaft section, wherein the first and second pressure applying occluding elements are pivotally secured to the respective first and second distal shaft sections and are adapted for pivoting independently of one another; and c. a connection between the first and second occluding members which is configured to adjust spacing between the first and second pressure applying occluding elements to press the pressure applying occluding elements against the patient's vaginal wall to occlude underlying uterine arteries.

2. The intravaginal occlusion device of claim 1 wherein the second occluding member has a second mechanism to distally extend at least part of the second pressure applying occluding element from a first position closer to the second operative proximal shaft section to a second position further away from the second operative proximal shaft section, wherein the first and second mechanisms to distally extend operate independently of one another so that the first and second pressure applying occluding elements are distally extendable independently of one another.

3. The intravaginal occlusion device of claim 1 wherein the connection between the first and second occluding members is a pivotal connection.

4. The intravaginal occlusion device of claim 1 wherein each of the proximal shaft sections of the occluding members includes a finger engaging grip.

5. The intravaginal occlusion device of claim 1 wherein at least part of the first pressure applying occluding element is configured for positional adjustment in-line with the first distal shaft section.

6. The intravaginal occlusion device of claim 1 wherein at least part of the first pressure applying occluding element is configured for rotation within a plane at or near the first distal shaft section.

7. The intravaginal occlusion device of claim 1 wherein movement of the first mechanism to distally extend the first pressure applying occluding element between the first and second positions is effected by fluid under pressure.

8. The intravaginal occlusion device of claim 1 wherein at least one of the first and second pressure applying occluding elements is provided with a blood flow sensor for detecting the location of the patient's uterine artery.

9. The intravaginal occlusion device of claim 8 wherein the blood flow sensor is a Doppler crystal.

10. The intravaginal occlusion device of claim 9 wherein the Doppler crystal is mounted in the pressure applying surface of the occluding element.

11. The intravaginal occlusion device of claim 9 wherein the Doppler crystal has a direction of view away from the pressure applying surface of the occluding element.

12. The intravaginal device of claim 1 wherein the first pressure applying occluding element is distally extendable away from the first distal shaft section a distance of up to about one inch.

13. The intravaginal device of claim 1 wherein the first pressure applying occluding element is distally extendable about 0.25 to about 0.8 inch from the first distal shaft section.

14. The intravaginal occlusion device of claim 1 wherein the first pressure applying occluding element includes an occlusion bar with a pressure applying surface.

15. The intravaginal occlusion device of claim 14 wherein the occlusion bar has a pair of legs which extend from a surface opposite to the pressure applying surface.

16. The intravaginal occlusion device of claim 15 wherein the first distal shaft section has a pair of arms with recesses therein configured to receive the legs extending from the occlusion bar.

17. An intravaginal device for occluding a female patient's uterine arteries with an unsymmetrical anatomy to treat a uterine disorder, comprising:
a first occluding member having a first elongated shaft, a first operative proximal shaft section configured to extend out of the patient during treatment, a first distal shaft section with a first pressure applying occluding element secured to the first distal shaft section, and a first mechanism to distally extend at least part of the first pressure applying occluding element from a first position closer to the first operative proximal shaft section to a second position further away from the first operative proximal shaft section; and
a second occluding member having a second elongated shaft, a second operative proximal shaft section configured to extend out of the patient during treatment and a second distal shaft section with a second pressure applying occluding element secured to the second distal shaft section, wherein the second occluding member has a second mechanism to distally extend at least part of the second pressure applying occluding element from a first position closer to the second operative proximal shaft section to a second position further away from the second operative proximal shaft section; and
a connection between the first and second occluding members which is configured to adjust spacing between the first and second pressure applying occluding elements to press the pressure applying occluding elements against the patient's vaginal wall to occlude underlying uterine arteries, wherein the first pressure applying occluding element is pivotally connected to the distal shaft section of the first occluding member and the second pressure applying occluding element is pivotally connected to the distal shaft section of the second occluding member, and wherein the first and second pressure applying occluding elements are adapted to pivot independently of one another.

18. The intravaginal occlusion device of claim 17 wherein the first occluding member includes a third mechanism for selectively rotating the first pressure applying occluding element relative to the distal shaft section of the first occluding member and the second occluding member includes a fourth mechanism for selectively rotating the second pressure applying occluding element relative to the distal shaft section of the second occluding member, wherein the third and fourth mechanisms operate independently of one another so that the first and second pressure applying occluding elements are pivotable independently of one another.

19. An intravaginal device for occluding uterine arteries comprising:
a first occluding member having a first elongated shaft with a proximal end and a distal end, a first occluding element secured to the distal end of the first elongated shaft, the first occluding element having a first pressure applying surface at a distal end thereof, and a first extending actuator coupled with the first occluding element for selectively moving the first pressure applying surface distally away from the distal end of the first elongated shaft, wherein the first occluding element is pivotally connected with the distal end of the first elongated shaft and the device further comprises a rotating actuator coupled with the first occluding element for selectively rotating the first pressure applying surface through a range of angles relative to the first elongated shaft; and
a second occluding member having a second elongated shaft with a proximal end and a distal end, a second occluding element pivotally connected to the distal end of the second elongated shaft, the second occluding element having a second pressure applying surface at a distal end thereof, wherein the first and second occluding elements are adapted for pivoting independently of one another; and the first and second occluding members being coupled together for selectively adjusting spacing between the first and second pressure applying surfaces.

20. The devices as claimed in claim 19, further comprising a first blood flow sensor accessible at the first pressure applying surface.

21. The device as claimed in claim 19, wherein the second occluding member further comprises a second extending actuator coupled with the second occluding element for selectively moving the second pressure applying surface distally away from the proximal end of the second elongated shaft.

22. The device as claimed in claim 21, wherein the second occluding member further comprises a second rotating actuator coupled with the second occluding element for selectively rotating the second pressure applying surface through a range of angles relative to the second elongated shaft, wherein the first and second rotating actuators operate independently of one another so that the first and second pressure applying surfaces rotate independently of one another.

23. The device as claimed in claim 19, further comprising a second blood flow sensor accessible at the second pressure applying surface.

24. The device as claimed in claim 19, wherein the first and second elongated shafts of the first and second occluding members are pivotally connected together.

25. An intravaginal device for occluding uterine arteries comprising:
   the intravaginal device having a proximal end, a distal end, and a longitudinal axis extending between the proximal and distal ends;
   a first occluding member having a first elongated shaft and a first occluding element secured to the distal end of the first elongated shaft, the first occluding element having a first pressure applying surface at a distal end thereof, and a first extending actuator coupled with the first occluding element for selectively moving the first pressure applying surface between a first position closer to the proximal end of the device and a second position further away from the proximal end of the device; and
   a second occluding member having a second elongated shaft pivotally connected with the first elongated shaft, the second occluding member having a second occluding element secured to the distal end of the second elongated shaft, a second pressure applying surface at a distal end thereof, and a second extending actuator coupled with the second occluding element for selectively moving the second pressure applying surface between a first position closer to the proximal end of the device and a second position further away from the proximal end of the device, wherein the first occluding element is pivotally connected with the distal end of the first elongated shaft and the first occluding member further comprises a first rotating actuator coupled with the first occluding element for selectively rotating the first pressure applying surface through a range of angles relative to the first elongated shaft, and wherein the second occluding element is pivotally connected with the distal end of the second elongated shaft and the second occluding member further comprises a second rotating actuator coupled with the second occluding element for selectively rotating the second pressure applying surface through a range of angles relative to the second elongated shaft.

26. The device as claimed in claim 25, further comprising a first blood flow sensor accessible at the first pressure applying surface, and a second blood flow sensor accessible at the second pressure applying surface.

27. The device as claimed in claim 25, wherein the first and second occluding members are pivotally connected together for adjusting spacing between the first and second pressure applying surfaces.

28. The device as claimed in claim 25, wherein said first and second occluding elements are movable along the longitudinal axis of said device.

29. The device as claimed in claim 25, wherein said first and second occluding elements are movable independently of one another along the longitudinal axis of said device, and wherein the first and second rotating actuators operate independently of one another so that the first and second pressure applying surfaces are rotatable independently of one another.

* * * * *